United States Patent [19]

Vilhardt

[11] Patent Number: 4,871,542

[45] Date of Patent: Oct. 3, 1989

[54] METHOD AND APPARATUS USEFUL FOR DELIVERING MEDICINAL COMPOSITIONS INTO THE BLADDER AND URINARY TRACT

[75] Inventor: Hans Vilhardt, Espergarde, Denmark

[73] Assignee: Ferring Service Center, N.V., Netherlands Antilles

[21] Appl. No.: 57,298

[22] Filed: Apr. 30, 1987

[51] Int. Cl.[4] ............................. A61F 2/00; A61K 9/22
[52] U.S. Cl. ................................... 424/423; 424/425; 424/426; 604/892.1
[58] Field of Search ................. 424/425, 423, 426; 604/892.1

[56] References Cited

U.S. PATENT DOCUMENTS

| | | | |
|---|---|---|---|
| 3,247,066 | 4/1966 | Milosovich, Jr. | 167/82 |
| 3,710,795 | 1/1973 | Higuchi et al. | 128/260 |
| 3,737,521 | 6/1973 | Born | 424/22 |
| 3,760,805 | 9/1973 | Higuchi | 128/260 |
| 3,760,806 | 11/1973 | Leeper | 128/260 |
| 3,845,761 | 11/1974 | Zaffaroni | 128/130 |
| 3,865,108 | 2/1975 | Hartop | 128/260 |
| 3,887,699 | 6/1975 | Yolles | 424/19 |
| 3,921,636 | 11/1975 | Zaffaroni | 424/425 |
| 3,938,515 | 2/1976 | Leeper et al. | 128/260 |
| 3,946,734 | 4/1976 | Dedrick et al. | 128/260 |
| 3,948,254 | 4/1976 | Zaffaroni | 128/127 |
| 3,993,073 | 11/1976 | Zaffaroni | 128/260 |
| 4,055,178 | 10/1977 | Harrigan | 128/260 |
| 4,111,202 | 9/1978 | Theeuwes | 128/260 |
| 4,177,256 | 12/1979 | Theeuwes | 424/22 |
| 4,220,152 | 9/1980 | Dresback | 128/260 |
| 4,235,236 | 11/1980 | Theeuwes | 128/260 |
| 4,304,232 | 12/1981 | Michaels | 128/260 |
| 4,309,996 | 6/1982 | Theeuwes | 128/260 |
| 4,344,431 | 8/1982 | Yolles | 128/260 |
| 4,351,337 | 9/1982 | Sidman | 18/260 |
| 4,402,695 | 9/1983 | Wong | 604/892 |
| 4,434,153 | 2/1984 | Urquhart et al. | 424/22 |
| 4,455,144 | 6/1984 | Michaels | 604/892 |
| 4,484,921 | 11/1984 | Swanson et al. | 604/892 |
| 4,525,340 | 6/1985 | Lange et al. | 424/16 |
| 4,536,387 | 8/1985 | Sakamoto et al. | 424/426 |
| 4,619,913 | 10/1986 | Luck et al. | 424/425 X |
| 4,670,014 | 6/1987 | Huc et al. | 424/426 X |

Primary Examiner—Thurman K. Page
Attorney, Agent, or Firm—Hopgood, Calimafde, Kalil, Blaustein & Judlowe

[57] ABSTRACT

The present invention provides a method and an apparatus for delivering medicinals to animal or human bladders. The apparatus is a polymeric, minicellular container surrounding an internal reservoir which contains the medicinal. The apparatus delivers the medicinal to the bladder at a prolonged, continuous and controlled rate.

15 Claims, 3 Drawing Sheets

METHOD AND APPARATUS USEFUL FOR DELIVERING MEDICINAL COMPOSITIONS INTO THE BLADDER AND URINARY TRACT

BACKGROUND OF THE INVENTION

This invention relates to treatment of diseases of the bladder and urinary tract. More specifically, the invention is directed to a method of delivering medicinal compositions directly to the bladder at controlled rates.

Various modes for delivery of medicinals to the bladder and urinary tract are known in the art. Patients with cancer may, for example, be treated with chemotherapy, i.e., toxic agents which primarily destroy malignant cells. The drugs are normally administered as injections, but in the case of carcinoma of the urinary bladder, instillation of an anticancer or cystostatic agent directly into the cavity of the bladder is recommended. This is done by daily injections of the drug through a catheter which is introduced through the urethra.

The advantage of this focal treatment is that the drug is placed in direct contact with the malignant cells, whereas the drug concentration everywhere else in the body is minimal. This reduces the occurrence of general side effects. Although this principle holds true for any focal application of a drug, it is particularly pertinent when it comes to administration of drugs directly into the cavity of the bladder, because the permeability of compounds through the mucosal lining of the bladder is low.

The drawbacks of this type of focal treatment are that the patient must undergo daily catheterization of the bladder which is both costly and unpleasant and the treatment is inefficient because the drug stays in the bladder for only a few hours, i.e., until the next micturition or urination.

Another means of administering medicinals to the bladder and urinary tract is to take the medicinals orally. In such a case, the medicinals gradually pass from the kidney into the bladder. Antibiotics, e.g., sulphur drugs, or urinary tract antiseptics and anesthetics, e.g. pyridium, are administered in this manner. Uncertain drug levels may be obtained in this manner due to various rates of individual clearance of the medicinals through the kidneys. In the case of anesthetics, a significant period of time may pass before any relief from pain or discomfort is achieved.

The search has continued for new and improved methods of delivering drugs to the bladder and delivery devices used in those methods. This invention was made as a result of that search.

OBJECTS AND SUMMARY OF THE INVENTION

Accordingly, it is a general object of the present invention to avoid or substantially alleviate the above-identified problems of the prior art.

A more specific object of the present invention is to provide a method for effectively supplying medicinals or the like to the bladder or urinary tract.

A further object of this invention is to eliminate unwanted side effects associated with conventional methods of supplying medicinals to the bladder or urinary tract.

An additional object of this invention is eliminate the necessity of frequent administration of medicinals, thereby increasing regimen compliance and decreasing costs associated with treatment.

Still another object of this invention is to provide a delivery device useful for delivering medicinals to the bladder or urinary tract in an effective manner using a minimum of catheterization.

Yet another object of this invention is to increase the comfort level of a patient by eliminating pain, discomfort and embarrassment associated with frequent administration of medicinals or the like to a bladder or urinary tract.

Other objects and advantages of this invention will become apparent from the following summary of the invention and description of its preferred embodiments.

The present invention provides, in one aspect, a method for delivering medicinals to the bladder and urinary tract of an animal or human. This method comprises introducing into the bladder a porous, minicellular, polymeric container which acts as a reservoir for a medicinal or plurality of medicinals. The polymer is compatable with the tissues of living organisms when it is implanted and may be constructed from biodegradeable materials. The size of the minicellular pores regulates the diffusion of the medicinal. The device of this method can contain floatation means and may be formed into an O-shaped ring. The medicinal or medicinals or the like are kept in constant contact with the surrounding environment at a programmed or controlled rate of diffusion over a prolonged period of time. In another aspect of the invention the diffusion rate is controlled by an osmotic minipump.

In yet another aspect, the present invention provides a bladder or urinary tract medicinal delivery apparatus made from a polymeric minicellular porous tube which surrounds an internal reservoir containing a medicinal. The polymer may be made of polypropylene or a substance which may be biodegradeable. The apparatus may be fashioned into an O-shaped ring and contain a floatation means. Minicellular pores of varying size, an osmotic minipump, or a coating of material may regulate diffusion rates.

BRIEF DESCRIPTION OF THE DRAWINGS

The drawings illustrate various embodiments of the invention as follows.

DETAILED DESCRIPTION OF THE PREFERRED EMBODIMENT

Figure 1:
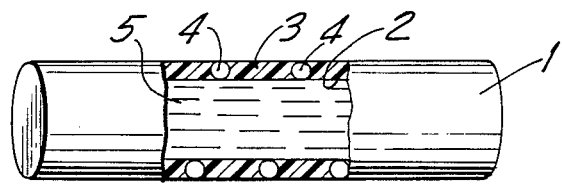
FIG. 1 is a side view of an apparatus useful for delivering medicinal compositions into the bladder and urinary tract and illustrates both an external and internal configuration of a tubular form of the apparatus wherein floatation means are in a wall.

The drawings are examples of various delivery devices of the invention but said examples are not to be considered as limiting. FIG. 1, an apparatus useful for delivering medicinal compositions into the bladder and urinary tract comprises external surface 1 composed of a polymeric, minicellular porous wall which is tube shaped. Internal surface 2 surrounds a reservoir 5 of medicinal. The apparatus of FIG. 1 has floatation means 4 located within a polymeric, minicellular porous wall 3.

Figure 2:
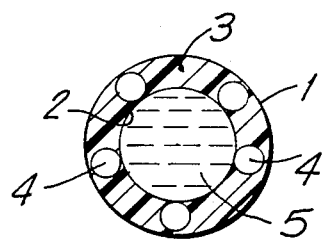
FIG. 2 is a cross sectional view of the apparatus of FIG. 1.

In FIG. 2, the apparatus of FIG. 1 is shown in cross section. Internal surface 2 surrounds a reservoir 5 of medicinal. Located within a polymeric, minicellular porous wall 3 is floatation means 4. Internal surface 2 contacts the medicinal in reservoir 5 and the medicinal diffuses through wall 3.

Figure 3:
FIG. 3 is a side view of an apparatus useful for delivering medicinal compositions into the bladder and urinary tract and illustrates both an external and internal configuration of a tubular form of the apparatus wherein floatation means are in a reservoir.
Figure 4:
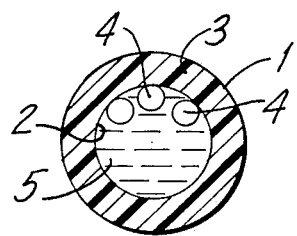
FIG. 4 is a cross sectional view of the apparatus of FIG. 3.

In FIG. 3, an apparatus useful for delivering medicinal compositions into the bladder and urinary tract comprises external surface 1 which includes polymeric, minicellular porous wall 3 which embodies a tube configuration. Internal surface 2 contacts a medicinal contained in reservoir 5. Floatation means 4 is found within reservoir 5. FIG. 4 is a cross-sectional view of the apparatus of FIG. 3.

Figure 5:
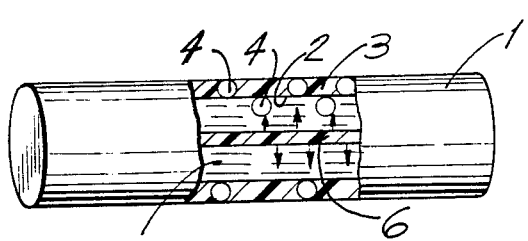
FIG. 5 is a side view of an apparatus useful for delivering medicinal compositions into the bladder and urinary tract and illustrates both an external and internal configuration of a tubular form with an osmotic minipump version of the apparatus.
Figure 6:
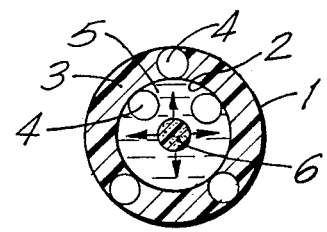
FIG. 6 is a cross sectional view of the apparatus of FIG. 5.

FIG. 5 shows an apparatus useful for delivering medicinal compositions into the bladder and urinary tract. It is composed of external surface 1 which includes polymeric, minicellular porous wall 3 which embodies a tube configuration. Internal surface 2 contacts a medicinal within reservoir 5. The medicinal diffuses through wall 3. Floatation means 4 is located in wall 3 as well as in reservoir 5. Osmotic minipump 6 absorbs liquid and expands, thus pushing said medicinal through wall 3 at a controlled and continuous rate. FIG. 6 is a cross sectional view of the apparatus of FIG. 5.

Figure 7:
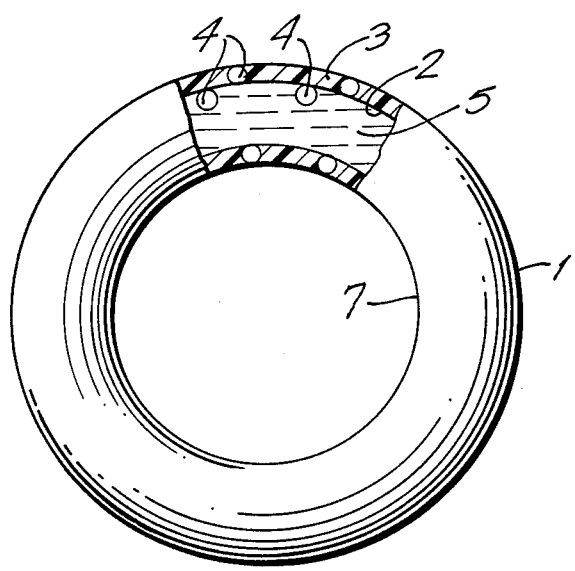
FIG. 7 is a top view of an apparatus useful for delivering medicinal compositions into the bladder and urinary tract and illustrates both an external and internal configuration of a ring shaped form of the apparatus.

FIG. 7 illustrates an apparatus useful for delivering medicinal compositions into the bladder and urinary tract. It is composed of external surface 1 which includes polymeric, minicellular porous wall 3 which embodies an O-ring configuration. The O-ring configuration is sized, structured and adapted for easy placement, prolonged retention, and easy removal from the bladder. Wall 3 surrounds and contacts reservoir 5 containing a medicinal via inner surface 2. Floatation means 4 is located in both reservoir 5 and wall 3. Floatation means 4 prevents obstruction of the bladder during urination by keeping said apparatus floating high above the bladder outlet. Said apparatus may be removed by hooking around inner external surface 7 and pulling the apparatus out through a cystoscope.

Figure 8:
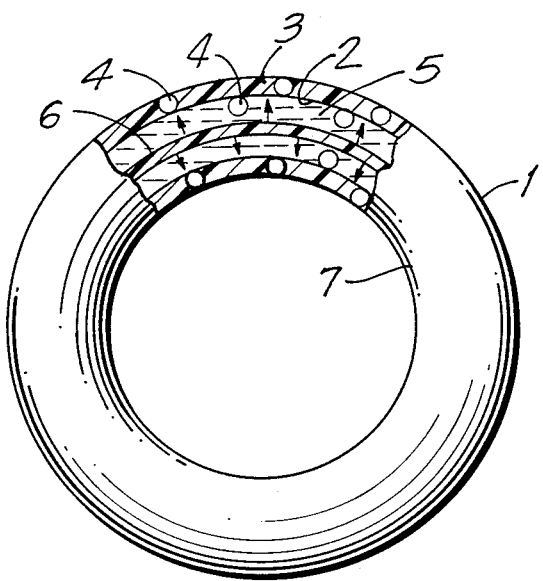
FIG. 8 is a top view of an apparatus useful for delivering medicinal compositions to the bladder and urinary tract which illustrates both an external and internal configuration of a ring shaped form of an osmotic pump version of the apparatus.

FIG. 8 is an apparatus useful for delivering medicinal compositions into the bladder and urinary tract. It includes external surface 1 composed of polymeric minicellular porous wall 3 which embodies an O-shaped ring. Wall 3 surrounds and contacts reservoir 5 via inner surface 2. Floatation means 4 is located both in reservoir 5 and in wall 3. Osmotic minipump 6 absorbs liquid and expands, thus forcing the medicinal through wall 3 at a controlled and continuous rate.

As illustrated above, this method of delivering medicinals to the bladder makes use of a polymeric container surrounding a reservoir of a medicinal agent. In the following description and claims, the term "medicinal" is used in its broadest sense and it includes any substance or mixture of substances which may have any clinical use. For convenience, the implant device or method of using said device will be described in terms of containing a medicinal, although it is to be understood that it may also contain a drug or a diagnostic agent such as a releasable dye which has no biological activity per se. Thus, in its broadest aspect, the method of delivery may be defined as the release of any substance, which may or may not exhibit biological activity.

Medicinals that can be used in this invention are anticancer agents, hormones, anesthetics, antiseptics, antibacterials, antibiotics, antivirals, and antimicrobials. The medicinals may be in the form of dry substance in aqueous solution, in alcoholic solution or contained in microcrystals, microspheres or liposomes. A more complete recitation of various medicinals is disclosed in Goodman and Gilman, The Pharmacological Basis of Therapeutics, 7th ed. 1985, the entire disclosure of which is hereby incorporated by reference.

In accordance with the above described principles, a plastic or polymeric device containing a medicinal is introduced into the bladder via a catheter. The nature of the plastic or polymer used is such that the medicinal agent is released into the bladder at a rate determined by the characteristics of the plastic used. Thus, by choosing a microporous wall material, and a release rate controlling pore size, the rate of passage of medicinal through the pores may be controlled to a high degree of specificity. Any suitable polymeric composition may be incorporated to achieve the objects of this invention. Examples include polypropylene, polyethylene, polystyrol (polystyrene), condensation polymers such as polyamide and copolymers, and polyvinyls.

In one embodiment of the invention, a plastic in the form of soft polypropylene tubing of various diameters is used. The wall of the tubing consists of mini-cells interconnected by small pores. When the lumen of the tubing is filled with a solution containing a given medicinal or chemical agent and the tubing is placed in an aqueous medium, such as urine, the agent will start to penetrate the wall of the tubing to enter the aqueous surroundings. The rate of diffusion for a given substance is determined by the size of the mini-cells and the pores. This embodiment may be called the "accurel principle".

In another embodiment of the invention, an osmotic minipump principle is employed. This embodiment also employs a sealed plastic tubing with a porous wall. In addition to the medicinal agent, the interior of the tubing contains an isolated compartment containing a solution of osmotically active particles. When placed in an aqueous medium, the osmotic compartment will absorb or imbibe water and expand, thereby slowly pressing out the medicinal agent from the lumen of the tubing to the aqueous surroundings. This principle has been used previously in the gastrointestinal tract, the vagina and the ano-rectal passageway as shown in U.S. Pat. Nos. 4,235,236 and 4,309,996.

Both the accurel and minipump principles provide for release of medicinals over a prolonged period of time (one day or more). While the accurel tubing releases the medicinal at a rate which decreases with time, the minipump will release the medicinal at a constant rate. However, the accurel tubing may be coated with a material (e.g. colloidion) which will act as a rate limiting step in the diffusion of the drug contained in the tubing thereby creating zero-order kinetics, i.e. a release of drug at a constant rate. This can be contrasted to a reaction involving first order kinetics that may be defined as one in which the rate of reaction is directly proportional to the concentration of the reacting substance.

In a preferred embodiment, the tubing is made to avoid obstruction of the outlet of the bladder during micturition. This may be accomplished in several ways. For example, the tubing may be formed as an 0-shaped ring which, because of its shape, tends not to block the outlet from the bladder. Additionally or alternatively, sealed air bubbles may be introduced in any number of places along the tubing or in the reservoir, thus allowing the tubing to float on top of the urine in the bladder. Since the outlet from the bladder is situated at the bottom of the bladder cavity, obstruction would not take place during micturition. Another means of avoiding obstruction may be achieved by using polymeric compositions that have a high degree of buoyancy in aqueous solutions. This buoyancy causes the medicinal container to rise to the top of the urine and achieve the same obstruction avoidance effect as the air bubble floatation means.

The plastic devices should be removed from the bladder when they have discharged their load of medicinal agent. The O-shape of the device makes it easy to catch by means of a cystoscope and the use of soft, flexible polymeric material in construction of the device allows it to be folded when retracted through a cystoscope. The problem of removal of the device may be simplified further by using a material which dissolves in an aqueous environment (e.g. urine). Any suitable biodegradable material may be incorporated, such as that disclosed, for example, in U.S. Pat. No. 4,351,337, the entire disclosure of which is hereby incorporated by reference. Depending upon the material used in such a device placed in the bladder, the agent will be released into the bladder over a prolonged period of time.

The administration and dosages of the various medicinals which may be used in this invention are known to those skilled in the art.

While the above described apparatus is advantageously used in the bladder, it may also be used in any organ which has a cavity, such as the uterine cavity, at any cancer site, or in the stomach at a cancer site. The apparatus may be adapted to treat any condition, curable by means of chemical therapy.

The present invention is illustrated by the following Examples. All parts and percentages in the Examples as well as in the specification and claims are by weight unless specified otherwise.

EXAMPLE I

This example illustrates the method of the present invention using accurel tubing filled with Mytomycin C, an anticancer drug.

Accurel polypropylene tubing, with an inner diameter of 1.3 mm, an outer diameter of 2.6 mm, a void volume of 75%, and a maximal pore diameter of 0.5 micron, is obtained from Enka Research Institute, Obernburg, West Germany. Before use, the tubing is placed in ethanol under vacuum followed by immersion in water.

Mitomycin C (commercially available from Kyowa Company of Japan) is obtained as a dry substance with a 24 fold excess of NaCl as carrier substance. Spectrophotometric scanning of an aqueous solution of this product showed an absorption maximum at 216 nm. Based on this, a standard curve is produced over the range of 0.2 $\mu$g/ml to 10 $\mu$g/ml of Mytomycin.

Twenty milligrams of Mitomycin is dissolved in 2 ml of distilled water and 800 $\mu$l of this is introduced in 3×10 cm of accurel tubing. The filled tubes are then heat sealed using a soldering iron and placed in a container with 7 ml of distilled water maintained at 37° C. The water is quantitatively removed and replaced with fresh water every 24 hours for 7 days. The concentration of Mitomycin in the removed water is determined at 216 nm.

Over a period of 7 days, Mitomycin is released from the tubing by simple first order kinetics. Other curves that represent drug concentration over time may be obtained by changing the concentration of Mitomycin in the tubing or by selecting a different accurel product, which will either enhance or reduce the rate of release of Mitomycin.

EXAMPLE II

This example illustrates the method of the present invention implemented with the use of an osmotic minipump and Mitomycin C.

Alzet osmotic minipump Model 2002, obtained from Alza Co., USA, is filled with 200 ml of Mitomycin C (10 mg/ml), obtained from Kyowa Company of Japan.

The pump loaded with Mitomycin is placed in a tube containing 5 ml of 0.9% NaCl and is kept at 37° C. The water is quantitatively removed and replaced with fresh saline every 24 hours for 7 days. The concentration of Mitomycin in the removed saline is determined at 216 nm.

Over a period of 7 days, Mitomycin C is released from the minipump at constant rate, giving a nearly constant concentration of Mitomycin in the saline solution.

The release rate may be changed by changing the concentration of Mitomycin in the pump and/or by using a different minipump model.

The principles, preferred embodiments and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of this invention.

I claim:

1. A method for delivering medicinals to animal or human bladders and urinary tracts which comprises:
   inserting into said bladder a polymeric, minicellular porous container, said container comprising an internal reservoir containing said medicinal and a flotation means effective to keep said container floating above the bladder outlet, wherein
   said medicinal diffuses through the pores of said container and into said bladder and urinary tract in an effective amount at a programmed, continuous, and controlled rate.

2. The method of claim 1 wherein the size of the minicellular pores regulates diffusion of the medicinal.

3. The method of claim 1 wherein the floatation means is an air bubble or series of air bubbles.

4. The method of claim 1 wherein the polymeric, minicellular porous container is formed into an O-shaped ring.

5. The method of claim 1 wherein the polymeric, minicellular porous container is biodegradable.

6. The method of claim 1 wherein the polymeric, minicellular porous container is made of polypropylene.

7. The method of claim 1 wherein the medicinal is selected from the group consisting of anticancer agents, hormones, anesthetics, antiseptics, antibacterials, antibiotics, antivirals, antimicrobials, and diagnostics.

8. The method of claim 1 wherein the medicinal is Mitomycin C.

9. A method of delivering medicinals to animal or human bladders and urinary tracts which comprises:
   a. inserting a sealed polymeric container with a porous wall containing said medicinal and an isolated compartment containing a solution of osmotically active particles into the bladder;
   b. contacting said osmotically active particles with a liquid such that the osmotically active particles imbibe the liquid and expand, thereby pressing the medicinal out of said sealed polymeric container; and
   c. maintaining the medicinal in the bladder at a programmed, continuous and controlled rate.

10. The method of claim 9 wherein the device is constructed from buoyant material.

11. The method of claim 9 wherein said device contains a floatation means.

12. The method of claim 11 wherein said floatation means is an air bubble or series of air bubbles.

13. The method of claim 9 wherein said device is formed into an O-shaped ring.

14. The method of claim 9 wherein said device is made of a biodegradable material.

15. The method of claim 9 wherein the medicinal is selected from the group consisting of anticancer agents, hormones, anesthetics, antiseptics, antibacterials, antibiotics, antivirals, antimicrobials, and diagnostics.

* * * * *